United States Patent [19]

Edgren

[11] 4,390,531

[45] Jun. 28, 1983

[54] METHOD OF CONTRACEPTION USING PEAK PROGESTOGEN DOSAGE

[75] Inventor: Richard A. Edgren, Woodside, Calif.

[73] Assignee: Syntex Pharmaceuticals International Ltd., Hamilton, Bermuda

[21] Appl. No.: 291,533

[22] Filed: Aug. 10, 1981

[51] Int. Cl.$^3$ ..................... A01N 45/00; A61K 31/56
[52] U.S. Cl. .................................................. 424/239
[58] Field of Search ........................... 424/239; 20/42

[56] References Cited

U.S. PATENT DOCUMENTS

| 3,568,828 | 3/1971 | Lerner | 424/240 |
| 4,143,136 | 3/1979 | De Jagie et al. | 424/240 |
| 4,292,315 | 9/1981 | Vorys | 424/240 |

Primary Examiner—Elbert L. Roberts
Attorney, Agent, or Firm—Tom M. Moran; Alan M. Krubiner

[57] ABSTRACT

A method of contraception and a pharmaceutical package for effecting the method are disclosed. The method comprises a three phase sequence of estrogen/progestogen administration which is a daily sequence of unit dosages over a repeating cycle, which dosage sequence comprises, for one cycle:

(a) administering, as phase one, about 20–40 µg of ethinyl estradiol, (or of other estrogen in an amount sufficient to result in an equivalent effect) and about 0.3–0.8 mg of norethindrone (or of other progestogen in an amount sufficient to result in an equivalent effect) each day for 5–8 days, followed by;

(b) administering, as phase two, the same dosage of estrogen and twice the dosage of progestogen each day as was administered each day in phase one, for 7–11 days, followed by;

(c) administering, as phase three, the same dosage of estrogen and the same dosage of progestogen each day as was administered each day in phase one, for 3–7 days, followed by;

(d) administering, as phase four, no therapeutically active dosage, i.e. either no treatment or a placebo each day for 6–8 days, with the proviso that the total number of days in phases one through three is 21.

9 Claims, No Drawings

METHOD OF CONTRACEPTION USING PEAK PROGESTOGEN DOSAGE

BACKGROUND OF THE INVENTION

The present invention relates to novel methods and articles of manufacture which are packages containing compositions useful for effecting contraception in the human female. More particularly, the invention is directed to achieving contraception by administering a sequential dose of estrogen and progestogen, which includes a peak dosage of progestogen at approximately the mid-point of the menstrual cycle.

A number of regimens for controlling ovulation and conception by administering hormones are known, and are available commercially. Some of these are based on consistent dosage, throughout the administration period, of either estrogen or progestogen or both. Others are directed to biphasic treatments whereby the amounts of either or both of these hormones are increased or decreased at some point during the cycle. Closest to the regimen of the present invention are those administration programs which involve both progestogen and estrogen, and vary the amounts of either or both hormones such that a three-phase program is maintained. Methods of contraception which fit this description are found in U.S. Pat. Nos. 3,795,734 to American Home Products; 4,066,757 to Ortho; 3,957,982 to Schering A. G.; and German Pat. No. 2,431,704 to Asche. Of the aforementioned patents, that closest to the present invention is the Schering patent which describes a peak dosage of estrogen at the middle of the administration interval.

The present invention is designed so as to minimize the side effect of breakthrough bleeding by optimizing the amount of progestogen administered at the mid-point of the cycle.

The present invention also provides a "rest period" wherein no hormones are administered. Further, by peaking the dose of progestogen rather than estrogen, the total estrogen needed to be administered is minimized.

SUMMARY OF THE INVENTION

The present invention relates to a method for contraception in a female human, which method comprises administering to a subject in need of, or desiring, such an effect, a daily sequence of unit dosages over a repeating cycle, which dosage sequence comprises, for one cycle:

(a) administering, as phase one, about 20–40 μg of ethinyl estradiol, (or of other estrogen in an amount sufficient to result in an equivalent effect) and about 0.3–0.8 mg of norethindrone (or of other progestogen in an amount sufficient to result in an equivalent effect) each day for 5–8 days, followed by;

(b) administering, as phase two, the same dosage of estrogen and twice the dosage of progestogen each day as was administered each day in phase one, for 7–11 days, followed by;

(c) administering, as phase three, the same dosage of estrogen and the same dosage of progestogen each day as was administered each day in phase one, for 3–7 days, followed by;

(d) administering, as phase four, no therapeutically active dosage, i.e. either no treatment or a placebo each day for 6–8 days, with the proviso that the total number of days in phases one through three is 21.

Another aspect of the invention relates to a pharmaceutical package designed to effect the aforesaid method.

DETAILED DESCRIPTION OF THE INVENTION

Definitions

As used herein:

"Menstrual cycle" or "cycle" refers to the well-known and repetatively occurring menstrual sequence in the pre-menopausal female, of 28 days typical duration.

"Day one" of said cycle is defined as the first day of menstruation, and the days are numbered sequentially thereafter until menstruation again occurs; normally 28 days in number, but in some cases slightly more or less.

"Estrogen" as described herein, can be selected from any of those materials commonly known as and referred to as estrogenic agents and which are produced during the menstrual cyclic of premenopausal female humans or which occur in other animals or plants, or compounds synthesized artificially which have similar effects. Typical estrogens which are applicable to the present invention include, for example, ethinyl estradiol, mestranol, conjugated estrogens, stilbesterol, or various synthetic estrogens.

"Progestogen" refers to any compound which exhibits progestational activity analogous to that of progesterone. Typical progestogens which are effective in the present invention include, for example, norethynodrel, norgestrel, norethindrone acetate, or ethynodiol diacetate.

"Approximately equal" means that the percent difference between two amounts is 10% or less. "Twice" or "two times" includes the same percentage discrepancy.

Formulations, Sequence and Preferred Embodiments

The administration of the estrogens and progestogens of the present invention is kept at a level which is effective in achieving contraception in the subject. It is not clear at present, the exact mechanism of the workings of either of these two hormonal agents, however it is understood that their effects are, in somes sense, in opposition to each other. It is further understood, that it is desirable to keep the amount of artificially administrered hormones of this or any other type at a minimum. Therefore, the dosage levels are designed to maintain an effective level for the purpose of contraception, with a minimum of any other effects.

Since the normal cycle is 28 days, a preferred timing of the sequence would aim for repeating a cycle of that length. This is particularly important in a method of contraception, since the occurrence of menstruation constitutes evidence to the subject that the object of the administration has been achieved. Therefore, in a preferred regime, phase one would begin at between day 4 and day 6 of the menstrual cycle and would last 5–8 days, preferably 7 days, phase two would last from 7 to 11 days, preferably 7 to 9 days, phase three would last from 3 to 7 days, preferably 5 to 7 days, and phase four from 6 to 8 days, most preferably 7 days. The end of phase three, in any case, would conclude at approximately three days before the onset of menstruation. Thus, in any particular embodiment, the sum of the days of administration of therapeutically effective drugs would comprise a total of 21 days, with a 7 day interval during which placebos or no drug was administered.

It is to be understood, that the administration of the estrogen and progestogen in the components in the sequence described herein, would, in most women, synchronize their cycles to the 28 day regime. Thus, the method of the present invention may be applied to the general population of female humans, regardless of the regularity or irregularity of their menstrual cycles prior to practicing the method.

The method of the present invention is conventionally practiced by oral administration of the triphasic regime components, in suitable admixture with a pharmaceutically acceptable non-toxic carrier. Thus, the components can be appropriately compounded in any pharmaceutically acceptable non-toxic form, and can be packaged in any system convenient for proper delivery. For oral administration, a pharmaceutically acceptable non-toxic composition is formed by the incorporation of any of the normally employed excipients, such as, for example, pharmaceutical grades of manitol, lactose, starch, magnesium stearate, sodium saccharine, talcum, cellulose, glucose, sucrose, magnesium carbonate, and the like. Such compositions take the form of solutions, suspensions, tablets, pills, capsules, or powders. Such compositions may contain between about 0.1 and 95% active ingredient, preferably 1 to 70% active ingredient. See *Remington's Pharmaceutical Sciences,* Mack Publishing Company, Easton, Pa., 15th Edition, 1975, especially chapter 87. Dispensing systems useful herein include those which accommodate to conventional packaging equipment, such as transparent strip foil packages contiguously arranged in daily doses or other conventional means known in the art. A preferred estrogen is ethinyl estradiol, and a preferred progestogen is norethindrone.

The preferred levels of dosages for the appropriate phases of administration are as follows: for phase one, 5 to 8 days, approximately 35 $\mu$g of ethinyl estradiol (or of other estrogen in an amount sufficient to result in an equivalent effect) per day, and 0.50 mg of norethindrone, (or of other progestogen in an amount sufficient to result in an equivalent effect) per day, for phase two comprising 7 to 11 days the same amount of estrogen per day as in phase one, and approximately twice the amount of progestogen per day as in phase one, in phase three, comprising 3 to 7 days, the same amount of estrogen per day as in the previous two phases, and the same amount of progestogen as was administered in phase one; in phase four, a placebo or no therapeutically effective drug is administered.

There are two most favored specific regimes, in terms of days in given phases, which are as follows:

phase one comprises 7 days or 7 dosage units (day 5 through day 11);

phase two comprises 7 days or 7 dosage units (day 12 through day 18);

phase three comprises 7 days or 7 dosage units (day 19 through day 25);

phase four comprises 7 days or 7 dosage units (day 26 of one cycle through day 4 of the next).

The second regime which is especially favored is similar to the above described, except that phases one through four comprise 7, 9, 5 and 7 days or dosage units respectively. The second embodiment also begins on day 5, and continues accordingly.

The following examples serve to illustrate the invention and are not intended to limit it.

EXAMPLE 1

Compositions of unit dosage for one 28 day cycle

The following exemplifies the contents of tablets to be contained in a single package for the administration during one 28 day cycle.

| Day No. 5–11: Phase One - 7 tablets |
|---|
| 35 $\mu$g ethinyl estradiol, ultramicronized to average 3$\mu$ particle size |
| 0.5 mg norethindrone |
| 33.5 mg lactose |
| 17.2 mg cornstarch |
| 2.1 mg polyvinylpyrrolidone |
| 1.7 mg talc |
| 55.0 mg total weight which is supplemented to about 90 mg with a customary sugar mixture |

| Day No. 12–18: Phase Two - 7 tablets |
|---|
| 35 $\mu$g ethinyl estradiol, ultramicronized to average 3$\mu$ particle size |
| 1.0 mg norethindrone |
| 33.0 mg lactose |
| 17.2 mg cornstarch |
| 2.1 mg polyvinylpyrrolidone |
| 1.7 mg talc |
| 55.0 mg total weight which is supplemented to about 90 mg with a customary sugar mixture |

| Day No. 19–25: Phase Three - 7 tablets |
|---|
| 35 $\mu$g ethinyl estradiol, ultramicronized to average 3$\mu$ particle size |
| 0.5 mg norethindrone |
| 33.5 mg lactose |
| 17.2 mg cornstarch |
| 2.1 mg polyvinylpyrrolidone |
| 1.7 mg talc |
| 55.0 mg total weight which is supplemented to about 90 mg with a customary sugar mixture |

| Day No. 26–28, and Day 1–4 of subsequent cycle: Phase Four - 7 tablets |
|---|
| 34.0 mg lactose |
| 17.2 mg cornstarch |
| 2.1 mg polyvinylpyrrolidone |
| 1.7 mg talc |
| 55.0 mg total weight which is supplemented to about 90 mg with a customary sugar mixture |

EXAMPLE 2

Sample package and insert (directions) for the Composition regime of Example 1

The following packaging design and instructions is appropriate to the composition set of Example 1:

| INSIDE | OUTSIDE |
|---|---|
| (About these tablets) (Fold) | (Display) (Fold) |
| (How to use this pack) (Fold) | (Blank) (Fold) |
| (Flap out) - (Cut) | (Flap out) |
| (APPROX. 8 mm. HOLES SHOWING FOIL BACKING). | (Printed tablet order). (APPROX. 8 mm. HOLES SHOWING COLORED TABLETS THROUGH CLEAR BUBBLE). |

+ +

-continued

| INSIDE | | | | | | | OUTSIDE | | | | | | | |
|---|---|---|---|---|---|---|---|---|---|---|---|---|---|---|
| + | + | + | + | + | + | + | 1 | 2 | 3 | 4 | 5 | 6 | 7 | Day of Cycle |
| + | + | + | + | + | + |   |   |   |   |   | 1 | 2 | 3 | Pill No. |
|   |   | + | + | + | + | + | 8 | 9 | 10 | 11 | 12 | 13 | 14 | Day of Cycle |
|   |   |   |   |   |   |   | 4 | 5 | 6 | 7 | 8 | 9 | 10 | Pill No. |
|   |   |   |   |   |   |   | 15 | 16 | 17 | 18 | 19 | 20 | 21 | Day of Cycle |
|   |   |   |   |   |   |   | 11 | 12 | 13 | 14 | 15 | 16 | 17 | Pill No. |
|   |   |   |   |   |   |   | 22 | 23 | 24 | 25 | 26 | 27 | 28 | Day of Cycle |
|   |   |   |   |   |   |   | 18 | 19 | 20 | 21 | 22 | 23 | 24 | Pill No. |
|   |   |   |   |   |   |   | 1 | 2 | 3 | 4 | 5 | 6 | 7 | Day of Cycle |
|   |   |   |   |   |   |   | 25 | 26 | 27 | 28 |   |   |   | Pill No. |

ABOUT THESE TABLETS

- (The tablet set herein) is used to prevent conception and pregnancy.
- When treatment is first started, tingling of the breasts, slight nausea or occasional vaginal bleeding may occur—this should settle after a short time.
- If you have any unusual symptoms, contact your doctor.
- To be taken under medical supervision.

HOW TO USE THIS PACK

- IF YOU ARE MENSTRUATING REGULARLY take tablet No. 1 on the 5th day of your menstrual period. IF YOU ARE MENSTRUATING IRREGULARLY OR NOT AT ALL take the first tablet on a day suitable to yourself.
- Continue to take one tablet each day following the numerical order. Make a habit of taking your tablet at the same time of day (such as before going to bed).
- Try not to forget a tablet. If you forget your tablets on one or more days, discard the missed tablets and resume your course of therapy on the appropriate day.
- While taking (the tablet set herein) you should get a regular withdrawal bleeding the next day after tablet No. 24 each month. However, even if you do not get bleeding you should re-start your treatment the next day after tablet No. 28.

Alternatively, these instructions may be printed as a leaflet, and the package instructions modified as follows.

TRADEMARK

Before commencing treatment please read the enclosed instruction leaflet carefully. If you have any difficulties following the instructions, please ask your doctor for assistance.

DIRECTIONS

To remove a tablet, press firmly with your thumb on the appropriate clear plastic bubble. This may be helped by holding the card so that your other fingers surround the aluminium foil through which the tablet will emerge.

What is claimed is:

1. A method of contraception in the female human, which method comprises administering to a subject in need of, or desiring, such an effect, a daily sequence of unit dosages over a repeating cycle, which dosage sequence comprises, for one cycle:
    (a) administering, as phase one, for a period of 5–8 days, daily dosages of a combination of an estrogen and a progestogen, wherein the amounts of estrogen and progestogen correspond in estrogenic activity to about 20–40 μg of ethinyl estradiol, and in progestogenic activity to about 0.3–0.8 mg of norethindrone, followed by:
    (b) administering, as phase two, for a period of 7–11 days, the same dosage of estrogen and twice the dosage of progestogen each day as was administered in phase 1, followed by:
    (c) administering, as phase three, for a period of 3–7 days, the same dosage of estrogen and the same dosage of progestogen each day as was administered each day in phase one, followed by;
    (d) administering, as phase four, for a period of 6–8 days, no therapeutically active dosage, i.e. either no treatment or a placebo each day,
    with the proviso that the total number of days in phases one through three is 21.
2. A method of claim 1 wherein,
    the period specified in (a) is seven days;
    the period specified in (b) is seven days;
    the period specified in (c) is seven days;
    the period specified in (d) is seven days.
3. A method of claim 1 wherein,
    the period specified in (a) is seven days;
    the period specified in (b) is nine days;
    the period specified in (c) is five days;
    the period specified in (d) is seven days.
4. The method of claim 1 wherein, the dosages per day in (a) of estrogen and progestogen correspond in estrogenic activity to about 35 μg of ethiny estradiol and in progestogenic activity to about 0.50 mg of norethindrone.
5. The method of claim 2 wherein, the dosages per day in (a) of estrogen and progestogen correspond in estrogenic activity to about 35 μg of ethinyl estradiol and in progestogenic activity to about 0.50 mg of norethindrone.
6. The method of claim 3 wherein, the dosages per day in (a) of estrogen and progestogen correspond in estrogenic activity to about 35 μg of ethiny estradiol and in progestogenic activity to about 0.50 mg of norethindrone.
7. The method of claim 1 wherein the estrogen is ethinyl estradiol.
8. The method of claim 1 wherein the progestogen is norethindrone.
9. The method of claim 1 wherein the estrogen is ethinyl estradiol, and the progestogen is norethindrone.

* * * * *